(12) United States Patent
Taleb et al.

(10) Patent No.: US 11,631,181 B2
(45) Date of Patent: Apr. 18, 2023

(54) MULTIMODAL SELF-SUPERVISED LEARNING FOR IMAGE ANALYSIS

(71) Applicant: SAP SE, Walldorf (DE)

(72) Inventors: Aiham Taleb, Berlin (DE); Moin Nabi, Berlin (DE); Tassilo Klein, Berlin (DE)

(73) Assignee: SAP SE, Walldorf (DE)

( * ) Notice: Subject to any disclaimer, the term of this patent is extended or adjusted under 35 U.S.C. 154(b) by 289 days.

(21) Appl. No.: 17/010,719

(22) Filed: Sep. 2, 2020

(65) Prior Publication Data

US 2022/0067941 A1   Mar. 3, 2022

(51) Int. Cl.
*G06K 9/00* (2022.01)
*G06T 7/11* (2017.01)
*G06T 11/00* (2006.01)
*G06N 20/00* (2019.01)

(52) U.S. Cl.
CPC ........... *G06T 7/11* (2017.01); *G06N 20/00* (2019.01); *G06T 11/005* (2013.01); *G06T 2207/10048* (2013.01); *G06T 2207/10088* (2013.01); *G06T 2207/10132* (2013.01); *G06T 2207/20081* (2013.01)

(58) Field of Classification Search
None
See application file for complete search history.

(56) References Cited

PUBLICATIONS

Noroozi, Mehdi, and Paolo Favaro. "Unsupervised learning of visual representations by solving jigsaw puzzles (2016)." arXiv preprint arXiv:1603.09246 2. (Year: 2016).*

Pang, Kaiyue, et al. "Solving mixed-modal jigsaw puzzle for fine-grained sketch-based image retrieval." Proceedings of the IEEE/CVF Conference on Computer Vision and Pattern Recognition. 2020. (Year: 2020).*

Wei, Chen, et al. "Iterative reorganization with weak spatial constraints: Solving arbitrary jigsaw puzzles for unsupervised representation learning." Proceedings of the IEEE/CVF Conference on Computer Vision and Pattern Recognition. 2019. (Year: 2019).*

Adams, R. P. et al., "Ranking via sinkhorn propagation," arXiv preprint arXiv:1106.1925, 2011.

Albiol, A. et al., "Extending 2d deep learning architectures to 3d image segmentation problems," In Pre-Conference Proceedings of the 7th MICCAI BraTS Challenge, 2018.

Bakas, S. et al., Data Descriptor: Advancing the cancer genome atlas glioma mri collections with expert segmentation labels and radiomic features, Scientific Data, 4:170117 EP-, Sep. 2017.

(Continued)

*Primary Examiner* — Avinash Yentrapati
(74) *Attorney, Agent, or Firm* — Mintz Levin Cohn Ferris Glovsky and Popeo, P.C.

(57) ABSTRACT

A machine learning model may be trained on a first task of puzzle solving before being tuned on a second task of image analysis. The training of the machine learning model may be self-supervised whereas the tuning of the machine learning model may be supervised. The training data may include a puzzle generated to include multiple imaging modalities. The puzzle may be generated by shuffling a position of the pieces forming an original image. The machine learning model may be trained to perform the first task by reassembling the pieces in the puzzle to generate a reconstruction of the original image. Upon being trained to perform the first task and tuned to perform the second task, the machine learning model may be deployed to perform the second task. The second task may be an image segmentation task such as tumor segmentation and a regression task such as survival prediction.

16 Claims, 5 Drawing Sheets

(56) References Cited

PUBLICATIONS

Chang, Y.J. et al., "Automatic segmentation of brain tumor from 3d mr images using a 2d convolutional neural networks," In Pre-Conference Proceedings of the 7th MICCAI BraTS Challenge, 2018.
Gruenberg, K. et al., "Annotating Medical Image Data," pp. 45-67. Springer International Publishing, Cham, 2017.
Isensee, F. et al., "No new-net," arXiv:1809.10483, 2018.
Krizhevsky, K. et al., ImageNet classification with deep convolutional neural networks, In Advances in neural information processing systems, pp. 1097-1105, 2012.
Li, X. "Fused U-Net for brain tumor segmentation based on multimodal mr images," In Pre-Conference Proceedings of the 7th MICCAI BraTS Challenge, 2018.
Mena, G. et al., "Learning latent permutations with gumbel-sinkhorn networks," arXiv preprint arXiv:1802.08665, 2018.
Menze, B. H. et al., "The multimodal brain tumor image segmentation benchmark (brats)," IEEE Transactions on Medical Imaging, 34(10):1993-2024, 2015.
Noroozi, M. et al., "Unsupervised learning of visual representations by solving jigsaw puzzles," CoRR, abs/1603.09246, 2016.
Ronneberger, O. et al., "U-Net: Convolutional networks for biomedical image segmentation," In MICCAI, 2015.
Sinkhorn, R. "A relationship between arbitrary positive matrices and doubly stochastic matrices," The annals of mathematical statistics, 35(2):876-879, 1964.
Suter, Y. et al., "Deep learning versus classical regression for brain tumor patient survival prediction," arXiv:1811.04907, 2018.

\* cited by examiner

MULTIMODAL SELF-SUPERVISED LEARNING FOR IMAGE ANALYSIS

FIELD

The present disclosure generally relates to machine learning and more specifically to multimodal self-supervised learning for image analysis.

BACKGROUND

Machine learning models may be trained to perform a variety of cognitive tasks. For example, a machine learning model trained to perform image classification in which the machine learning model assigns, to an image, one or more labels corresponding to one or more objects depicted in the image. Training the machine learning model to perform image classification may include adjusting the machine learning model to minimize the errors present in the output of the machine learning model. For instance, training the machine learning model may include adjusting the weights applied by the machine learning model in order to minimize a quantity of incorrect labels assigned by the machine learning model.

SUMMARY

Methods, systems, and articles of manufacture, including computer program products, are provided for machine learning enabled image analysis. In one aspect, there is provided a system. The system may include at least one data processor and at least one memory. The at least one memory may store instructions that result in operations when executed by the at least one data processor. The operations may include: training, based at least on a first training data, a machine learning model to perform a first task of puzzle solving, the first training data including a puzzle that is generated to include a first piece comprising a first portion of a first image having a first imaging modality and a second piece comprising a second portion of a second image having a second imaging modality, the puzzle being generated by at least shuffling a respective position of the first piece and the second piece in a third image including the first piece and the second piece, and the machine learning model being trained to generate a reconstruction of the third image by at least reassembling the first piece and the second piece in the puzzle; tuning, based at least on a second training data, the machine learning model trained to perform the first task, the machine learning model being tuned to perform a second task of image analysis; and performing the second task by at least applying the machine learning model trained on the first task and tuned on the second task.

In some variations, one or more of the features disclosed herein including the following features can optionally be included in any feasible combination. The third image may be a ground-truth associated with the puzzle.

In some variations, the training of the machine learning model may include minimizing a mean squared error (MSE) between the third image and the reconstruction of the third image.

In some variations, the training of the machine learning model may be self-supervised and the tuning of the machine learning model may be supervised.

In some variations, the second training data may include one or more labeled training samples.

In some variations, the second task may be an image segmentation task or a regression task.

In some variations, the second task may be a tumor segmentation task that includes differentiating between a tumor and a normal tissue depicted in one or more images.

In some variations, the second task may be a survival prediction task that includes determining, based at least on one or more images, a quantity of time a patient associated with the one or more images is expected to survive.

In some variations, the first imaging modality and the second imaging modality may be a different one of a radiography, a magnetic resonance imaging (MRI), a nuclear imaging, an ultrasound, an elastogrpahy, a photoacoustic imaging, a tomography, an echocardiography, a functional near-infrared spectroscopy, and a magnetic particle imaging.

In some variations, the first task may be a proxy task and the second task may be a downstream task.

In another aspect, there is provided a method for machine learning enabled image analysis. The method may include: training, based at least on a first training data, a machine learning model to perform a first task of puzzle solving, the first training data including a puzzle that is generated to include a first piece comprising a first portion of a first image having a first imaging modality and a second piece comprising a second portion of a second image having a second imaging modality, the puzzle being generated by at least shuffling a respective position of the first piece and the second piece in a third image including the first piece and the second piece, and the machine learning model being trained to generate a reconstruction of the third image by at least reassembling the first piece and the second piece in the puzzle; tuning, based at least on a second training data, the machine learning model trained to perform the first task, the machine learning model being tuned to perform a second task of image analysis; and performing the second task by at least applying the machine learning model trained on the first task and tuned on the second task.

In some variations, one or more of the features disclosed herein including the following features can optionally be included in any feasible combination. The third image may be a ground-truth associated with the puzzle.

In some variations, the training of the machine learning model may include minimizing a mean squared error (MSE) between the third image and the reconstruction of the third image.

In some variations, the training of the machine learning model may be self-supervised and the tuning of the machine learning model may be supervised.

In some variations, the second training data may include one or more labeled training samples.

In some variations, the second task may be an image segmentation task or a regression task.

In some variations, the second task may be a tumor segmentation task that includes differentiating between a tumor and a normal tissue depicted in one or more images.

In some variations, the second task may be a survival prediction task that includes determining, based at least on one or more images, a quantity of time a patient associated with the one or more images is expected to survive.

In some variations, the first imaging modality and the second imaging modality may be a different one of a radiography, a magnetic resonance imaging (MRI), a nuclear imaging, an ultrasound, an elastogrpahy, a photoacoustic imaging, a tomography, an echocardiography, a functional near-infrared spectroscopy, and a magnetic particle imaging.

In another aspect, there is provided a computer program product that includes a non-transitory computer readable storage medium. The non-transitory computer-readable storage medium may include program code that causes operations when executed by at least one data processor. The operations may include: training, based at least on a first training data, a machine learning model to perform a first task of puzzle solving, the first training data including a puzzle that is generated to include a first piece comprising a first portion of a first image having a first imaging modality and a second piece comprising a second portion of a second image having a second imaging modality, the puzzle being generated by at least shuffling a respective position of the first piece and the second piece in a third image including the first piece and the second piece, and the machine learning model being trained to generate a reconstruction of the third image by at least reassembling the first piece and the second piece in the puzzle; tuning, based at least on a second training data, the machine learning model trained to perform the first task, the machine learning model being tuned to perform a second task of image analysis; and performing the second task by at least applying the machine learning model trained on the first task and tuned on the second task.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to machine learning enabled image analysis, it should be readily understood that such features are not intended to be limiting. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

Figure 1:
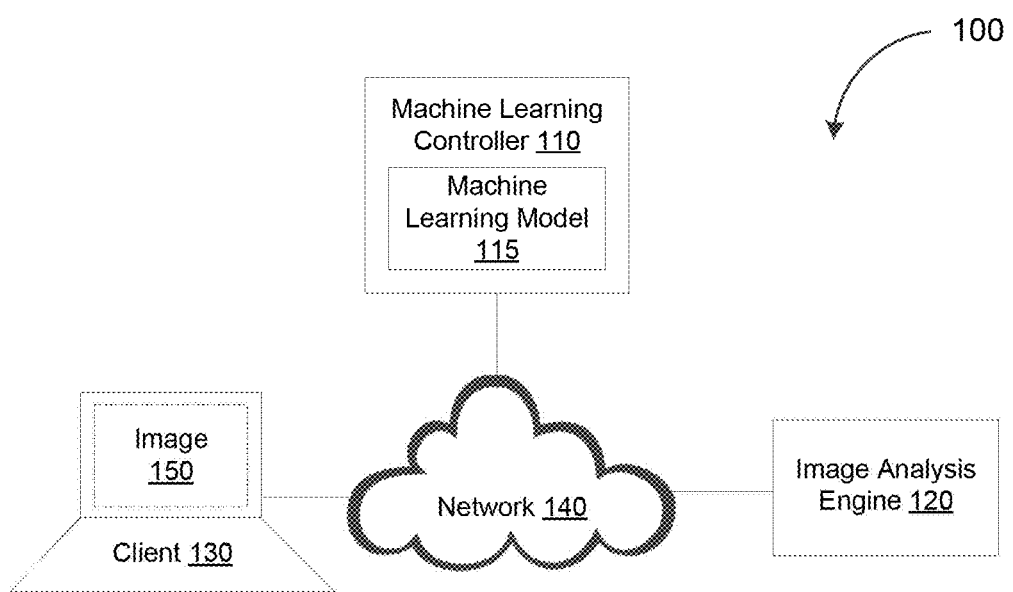
FIG. 1 depicts a system diagram illustrating a machine learning enabled image analysis system, in accordance with some example embodiments.

When practical, like labels are used to refer to same or similar items in the drawings.

DETAILED DESCRIPTION

A machine learning model may be trained to perform an image analysis task by at least subjecting the machine learning model to supervised learning. For example, the machine learning model may be trained to perform image classification, which may include assigning, to an image, one or more labels corresponding to one or more objects depicted in the image. Training the machine learning model for optimal performance may require a large corpus of labeled training samples, each of which including an image and at least one ground-truth label corresponding to a correct label for the text. However, generating a sufficiently large corpus of labeled training samples may require excessive resources. A large corpus of labeled trained example may be especially rare where expert annotations are required to provide the ground-truth labels for the training samples. As such, training the machine learning model in a supervised manner may often be impracticable.

In some example embodiments, a machine learning controller may train a machine learning model to perform an image analysis task by at least subjecting the machine learning model to self-supervised training. For example, the machine learning model may be trained, in a self-supervised manner, to perform a first task (e.g., a proxy task) before being subjected to a supervised tuning on a second task (e.g., downstream task). Accordingly, the machine learning controller may train the machine learning model to solve a puzzle, for example, a jigsaw puzzle, as a proxy for a downstream image analysis task such as, for example, image segmentation, regression, and/or the like. The corpus of training samples used to train the machine learning model to solve the puzzle may include ground-truth labels derived without expert annotations. Meanwhile, the quantity of training samples necessary to tune the machine learning model on the image analysis task may be minimal. As such, the machine learning model may be trained for optimal performance even when labeled training samples are scarce.

Training the machine learning model to perform the first task of puzzle solving may include training the machine learning model to reassemble shuffled portions of an image such that the image is restored to its original state. Each training sample used to train the machine learning model to solve a puzzle may include an image in which one or more portions of the image have been shuffled out of their original positions. Moreover, each training sample used to train the machine learning model to solve a puzzle may include a ground-truth label corresponding to the image in its original state. Deriving the ground-truth label for each training sample may not require any expert annotation. As such, training the machine learning model in a self-supervised manner to perform the first task may require less resources than training the machine learning model in a supervised manner.

In some example embodiments, in order to optimize the performance of the machine learning model when performing the second task (e.g., the downstream task), the training samples used to train the machine learning model to perform the first task (e.g., the proxy task) of puzzle solving may be generated to include multiple imaging modalities. For example, each training sample may be generated to include a first portion of a first image having a first image modality and a second portion of a second image having a second imaging modality. Examples of imaging modalities may include radiography, magnetic resonance imaging (MRI), nuclear imaging, ultrasound, elastogrpahy, photoacoustic imaging, tomography, echocardiography, functional near-infrared spectroscopy, and magnetic particle imaging. As such, training the machine learning model to solve a puzzle may include training the machine learning model to reassemble shuffled portions of an image having multiple imaging modalities such that the image is restored to its original state.

FIG. 1 depicts a system diagram illustrating an example of a machine learning enabled image analysis system 100, in accordance with some example embodiments. Referring to FIG. 1, the machine learning enabled image analysis system 100 may include a machine learning controller 110, an image analysis engine 120, and a client 130. The machine learning controller 110, the image analysis engine 120, and the client 103 may be communicatively coupled via a network 140. It should be appreciated that the client 130 may be a processor-based device including, for example, a smartphone, a tablet computer, a wearable apparatus, a virtual assistant, an Internet-of-Things (IoT) appliance, and/ or the like. The network 140 may be any wired network and/or a wireless network including, for example, a wide area network (WAN), a local area network (LAN), a virtual local area network (VLAN), a public land mobile network (PLMN), the Internet, and/or the like.

The machine learning controller 110 may train a machine learning model 115 to perform an image analysis task including, for example, image segmentation, regression, and/or the like. For instance, the machine learning controller 110 may train the machine learning model 115 to analyze medical imaging data such as scans (e.g., 2-dimensional scans, 3-dimensional scans, and/or the like) of anatomical features. Examples of image analysis tasks in a medical context may include tumor segmentation (e.g., brain tumor segmentation and/or the like) to separate tumor from normal tissue and survival prediction (e.g., regression).

Training the machine learning model 115 to perform the image analysis task in a supervised manner may require a large corpus of labeled training samples generated with expert annotations. As such, in some example embodiments, instead of training the machine learning model 115 to perform the image analysis task in a supervised manner, the machine learning controller 110 may subject the machine learning model 115 to self-supervised training. For example, the machine learning model 115 may be trained, in a self-supervised manner, to perform the first task (e.g., the proxy task) of puzzle solving (e.g., a jigsaw puzzle and/or the like) before the machine learning model 115 is tuned, in a supervised manner, to perform the second task (e.g., the downstream task) of image analysis. Doing so may minimize the quantity of labeled trained samples required to train the machine learning model 115 for optimal performance at least because the corpus of training samples used to train the machine learning model 115 to solve the puzzle may include ground-truth labels derived without expert annotations while the quantity of training samples necessary to tune the machine learning model 115 on the image analysis task may be minimal.

In some example embodiments, training the machine learning model 115 to perform the first task of puzzle solving may include training the machine learning mode 115 to reassemble shuffled portions of an image such that the image is restored to its original state. For example, each training sample used to train the machine learning model 115 to solve a puzzle may include an image in which one or more portions of the image have been shuffled out of their original positions. Moreover, each training sample used to train the machine learning model 115 to solve a puzzle may include a ground-truth label corresponding to the image in its original state, which may be derived without any expert annotation. As such, training the machine learning model 115 in a self-supervised manner to perform the first task of puzzle solving may require less resources, including expert annotated training samples, than training the machine learning model 115 in a supervised manner.

In some example embodiments, the training samples used to train the machine learning model 115 to perform the first task (e.g., the proxy task) of puzzle solving may be generated to include multiple imaging modalities. For example, each training sample may be generated to include a first portion of a first image having a first image modality and a second portion of a second image having a second imaging modality. Examples of imaging modalities may include radiography, magnetic resonance imaging (MRI), nuclear imaging, ultrasound, elastogrpahy, photoacoustic imaging, tomography, echocardiography, functional near-infrared spectroscopy, and magnetic particle imaging. Accordingly, training the machine learning model 115 to solve a puzzle may include training the machine learning model 115 to reassemble shuffled portions of an image having multiple imaging modalities such that the image is restored to its original state. Subjecting the machine learning model 115 to multimodal training samples may optimize the performance of the machine learning model 115 performing the second task (e.g., the downstream task) of image analysis.

Figure 2:
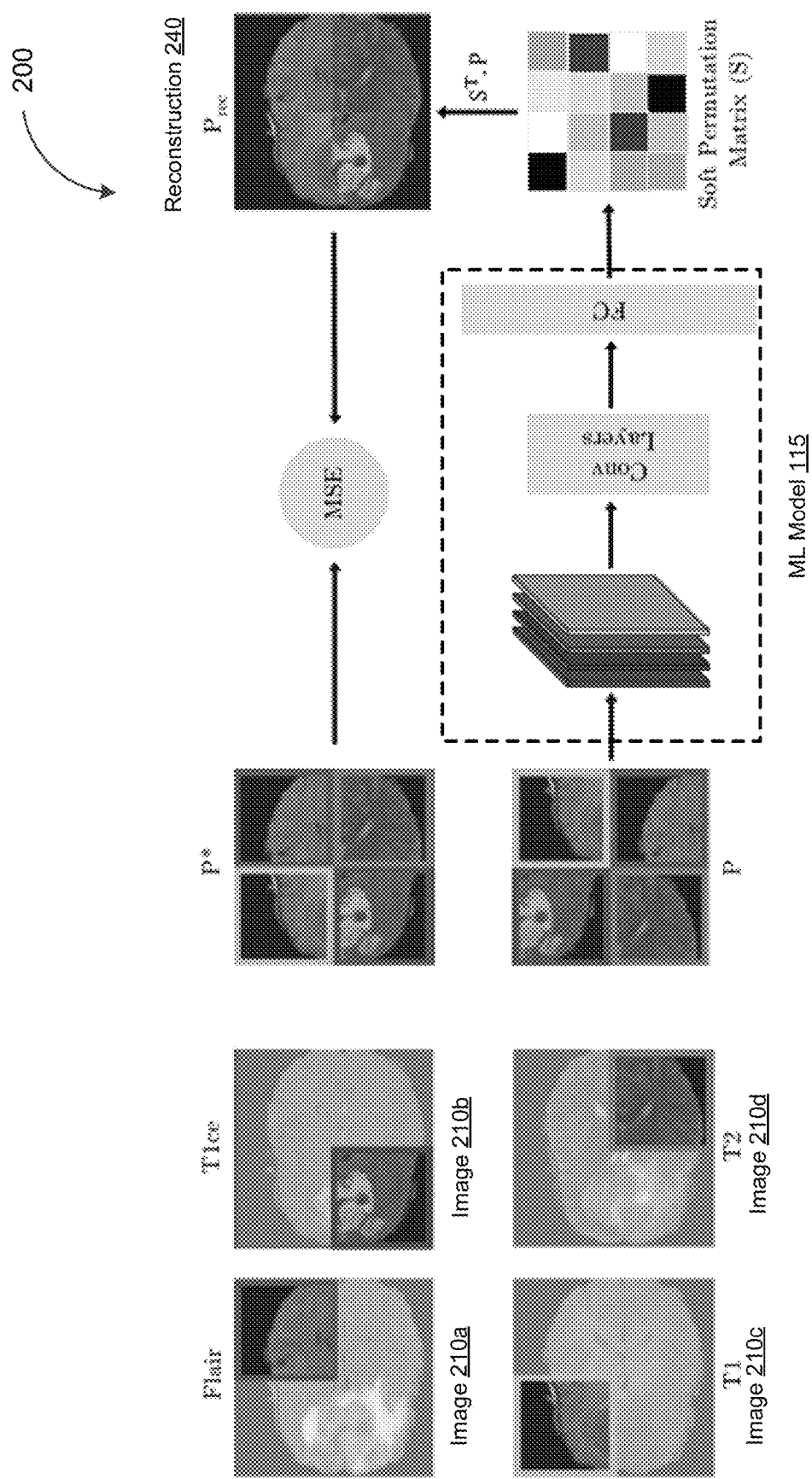
FIG. 2 depicts a schematic diagram illustrating an example of a process for training a machine learning model to perform an image analysis task, in accordance with some example embodiments.

To further illustrate, FIG. 2 depicts a schematic diagram illustrating an example of a process for training the machine learning model 115 to perform an image analysis task, in accordance with some example embodiments. The machine learning model 115 may, as noted, be trained in a self-supervised manner to perform the first task (e.g., the proxy task) of puzzle solving. Accordingly, as shown in FIG. 2, the corpus of training samples used to train the machine learning model 115 may include a puzzle P and a ground truth P*. The puzzle P may generated by shuffling one or more portions of an image out of their original positions whereas the ground truth P* may correspond to the image in its original state. As such, it should be appreciated that the ground truth P* of the puzzle P may be derived without expert annotations.

In some example embodiments, the puzzle P may be generated to include multiple imaging modalities including, for example, radiography, magnetic resonance imaging (MRI), nuclear imaging, ultrasound, elastogrpahy, photoacoustic imaging, tomography, echocardiography, functional near-infrared spectroscopy, magnetic particle imaging, and/ or the like. In the example shown in FIG. 2, the puzzle P may include a plurality of pieces including, for example, a first piece corresponding a first portion of a first image 210a having a first imaging modality (e.g., Fluid-attenuated inversion recovery (FLAIR)), a second piece corresponding to a second portion of a second image 210b having a second imaging modality (e.g., T1-weighted contrast-enhanced (T1CE) magnetic resonance imaging (MRI)), a third piece corresponding to a third portion of a third image 210c having a third imaging modality (e.g., T1-weighted magnetic resonance imaging (MRI)), and a fourth piece corresponding to a fourth portion of a fourth image 210d having a fourth imaging modality (e.g., T2-weighted magnetic resonance imaging (MRI)). Training the machine learning model 115 based on multimodal training samples may optimize the performance of the machine learning model 115 performing the second task (e.g., the downstream task) of image analysis.

Referring again to FIG. 2, solving the puzzle P may include reassembling the shuffled portions of the first image 210a, the second image 210b, the third image 210c, and the fourth image 210d forming the puzzle P to restore the image to its original state. For example, the portions of the first image 210a, the second image 210b, the third image 210c, and the fourth image 210d may be combined to form a fifth image corresponding to the ground truth P*. Generating the puzzle P may include shuffling the positions of the portions of the first image 210a, the second image 210b, the third image 210c, and/or the fourth image 210d in the fifth image. If C denotes the quantity of the pieces included in the puzzle P, then C! may denote the quantity of possible permutations of the C quantity of pieces in the puzzle P. Moreover, because each piece of the puzzle P may have one of an M quantity of imaging modalities, the complexity of solving the example of the puzzle P shown in FIG. 2 may be O(C!M).

Solving the puzzle P may become prohibitively expensive due to two growth factors in the solution space including the factorial growth in the quantity of permutations C! and the exponential growth in the quantity of modalities M. As such, in some example embodiments, the Sinkhorn operator may be applied in order to reduce the computational burden of solving the factorial factor associated with the quantity of permutations C!. Moreover, the machine learning model 115 may be implemented as a feed-forward network G configured to learn a modality agnostic representation of the puzzle P, thereby eliminating the exponential factor M while simultaneously learning a semantically rich representation of the puzzle P for the second task (e.g., the downstream task) of image analysis.

In some example embodiments, the non-differentiable parameterization of a permutation may be approximated in terms of a differentiable relaxation known as the Sinkhorn operator. While a permutation matrix may have a single entry of 1 in each row and each column, the Sinkhorn operator may iteratively normalize the rows and columns of any real-valued matrix to obtain a soft permutation matrix S. Accordingly, given a set of patch sets P=$p_1, p_2, \ldots, p_N$, the machine learning model 115 (e.g., the feedforward network G) may be trained to learn a mapping from the puzzle P to the corresponding ground truth P*. For example, each element in the puzzle P may be passed through the machine learning model 115, which may process every patch independently and produce a single output feature vector having a length N. The feature vectors for every region set in the puzzle P may be concatenated to form an N×N matrix, which may be passed to the Sinkhorn operator to obtain the soft permutation matrix S. As shown in FIG. 2, the training of the machine learning model 115 (e.g., the feedforward network G) may include minimizing the mean squared error (MSE) between the ground-truth P* and the reconstructed version of the puzzle P obtained by applying the soft permutation matrix S to the puzzle P (e.g., $S^T P$).

Once the machine learning model 115 is trained to perform the first task (e.g., the proxy task) of puzzle solving, the machine learning model 115 may be tuned on the second task (e.g., the downstream task) of image analysis. For example, the machine learning controller 110 may tune, in a supervised manner, the machine learning model 115 to perform an image analysis task such as image segmentation, regression, and/or the like. In some example embodiments, the machine learning controller 110 may, subsequent to training the machine learning model 115 to solve a puzzle (e.g., a jigsaw puzzle and/or the like), tune the machine learning model 115 to analyze medical imaging data such as scans (e.g., 2-dimensional scans, 3-dimensional scans, and/or the like) of anatomical features. As noted, examples of image analysis tasks in a medical context may include tumor segmentation (e.g., brain tumor segmentation and/or the like) to separate tumor from normal tissue and survival prediction (e.g., regression). Moreover, the machine learning model 115 tuned to perform image analysis may be deployed to the image analysis engine 120 where the machine learning model 115 may be applied to analyze, for example, an image 150 sent to the image analysis engine 120 by the client 130.

The performance of the machine learning model 115 trained on the first task of puzzle solving before being tuned on the second task of tumor segmentation (e.g., brain tumor segmentation and/or the like) may be comparable to the performance of a machine learning model (e.g., a convolutional neural network) trained to perform the tumor segment task in a supervised manner. Table 1 below depicts a comparison of the respective performances of the machine learning model 115 and various conventionally trained machine learning models. The performances of the machine learning model 115 and the conventionally trained machine learning models may be evaluated based on the respective Dice scores for whole tumor (WT), tumor core (TC), and enhanced tumor (ET). While the performances of the machine learning model 115 and the conventionally trained machine learning models may be comparable, it should be appreciated that the machine learning model 115 may achieve such performance with fewer resources including a minimal quantity of expert annotated training samples than the conventionally trained machine learning models.

TABLE 1

| Model | WT | TC | ET |
|---|---|---|---|
| Baseline (from scratch) | 80.76 | 77.07 | 67.77 |
| Li [7] | 88.30 | 78.80 | 72.00 |
| Albiol et al [2] | 87.20 | 76.00 | 75.10 |
| Chang er all [13] | 89.00 | 82.41 | 76.60 |
| Isensee et al [5] (3D U-Net) | 90.80 | 84.32 | 70.59 |
| Our Proposed Method | 89.67 | 83.73 | 78.54 |

Table 2 depicts a comparison of the respective performances of the machine learning model 115 and various conventionally trained machine learning models when performing the task of survival prediction (e.g., regression). As shown in Table 2, the machine learning model 115 trained on the first task of puzzle solving before being tuned on the second task of survival prediction (e.g., regression) may outperform the conventionally trained machine learning models.

TABLE 2

| Model | MSE |
|---|---|
| Baseline (from scratch) | 112,841 |
| CNN + age | 137,912 |
| Random Forest Reg | 152,130 |
| FeatNet + all features | 103,878 |
| Lin. Reg. + top 16 features | 99,370 |
| Our Proposed Method | 97,291 |

Figure 3:
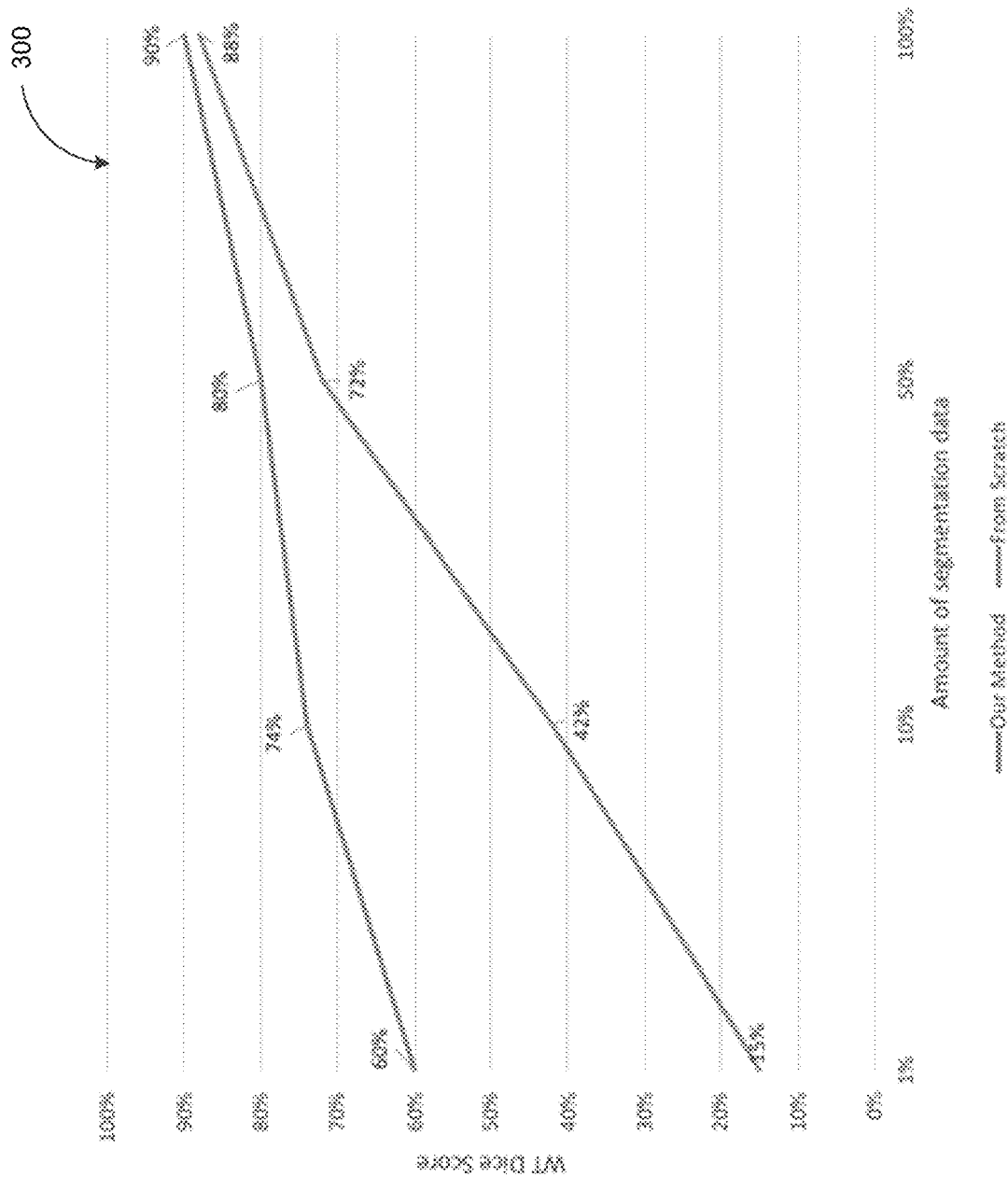
FIG. 3 depicts a graph illustrating a performance of a machine learning model trained to perform an image analysis task in a self-supervised manner relative to a performance of a conventionally trained machine learning model, in accordance with some example embodiments.

FIG. 3 depicts a graph 300 illustrating a performance of the machine learning model 115 relative to the performance of a conventionally trained machine learning model, in accordance with some example embodiments. The performance of the machine learning model 115 performing the second task (e.g., the downstream task) of image analysis may vary based on the quantity of labeled training samples used to tune the machine learning model 115 in the supervised manner. For example, the graph 300 depicts the performance of the machine learning model 115 performing the second task of tumor segmentation when the machine learning model 115 is tuned with various quantities of labeled training samples (e.g., 1%, 10%, 50%, and 100% of the total segmentation set size). Furthermore, the graph 300 depicts the performance of a conventionally trained machine learning model, which may be subject to supervised training on the tumor segmentation task directly without any self-supervised training on the first task of puzzle solving. As shown in FIG. 3, the machine learning model 115 may outperform the conventionally trained machine learning model in the task of tumor segmentation.

Figure 4:
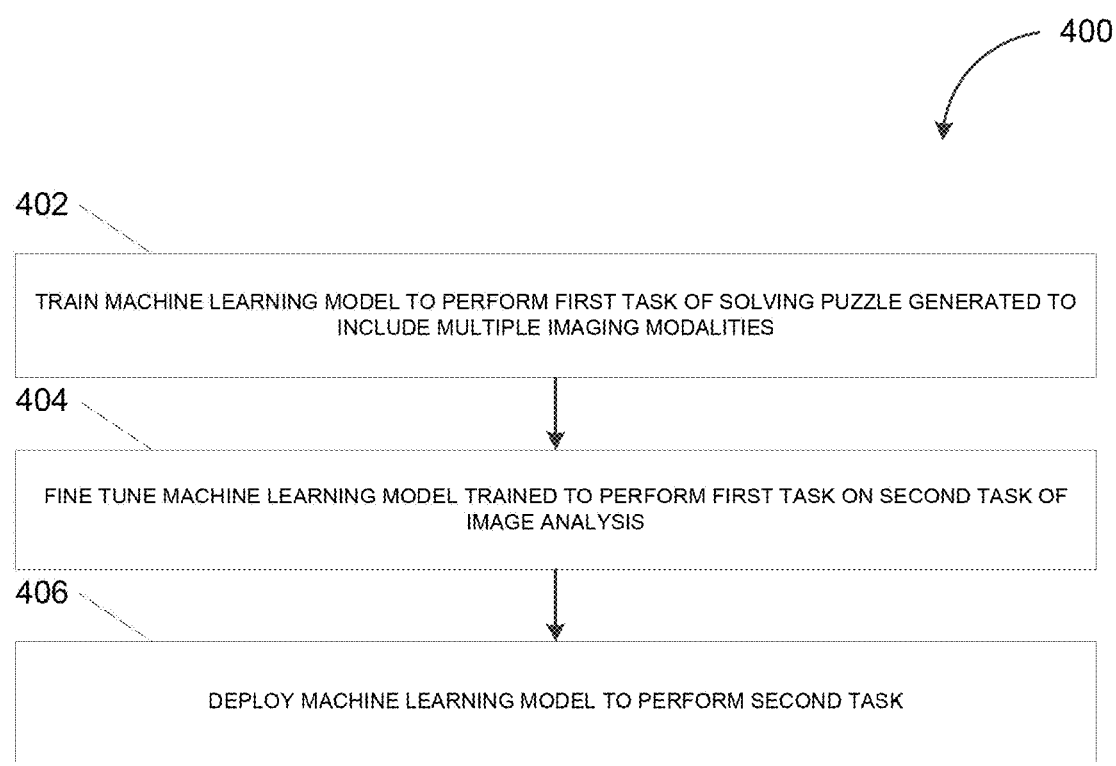
FIG. 4 depicts a flowchart illustrating an example of a process for machine learning enabled image analysis, in accordance with some example embodiments.

FIG. 4 depicts a flowchart illustrating a process 400 for machine learning enabled image analysis, in accordance with some example embodiments. Referring to FIGS. 1-4, the process 400 may be performed by the machine learning controller 110 in order to train, for example, the machine learning model 115 to perform an image analysis task such as image segmentation (e.g., tumor segmentation and/or the like) and regression (e.g., survival prediction and/or the like).

At 402, the machine learning controller 110 may train the machine learning model 115 to perform a first task of solving a puzzle generated to include multiple imaging modalities. In some example embodiments, the machine learning model 115 may be trained, in a self-supervised manner, to perform the proxy task of puzzle solving. For example, as shown in FIG. 2, the corpus of training samples used to train the machine learning model 11 to perform the proxy task may include the puzzle P generated by shuffling one or more portions of an image out of their original positions and the ground truth P* corresponding to the image in its original state. The machine learning model 115 may be trained in the self-supervised manner at least because the ground truth P* may be derived based on the puzzle P without any expert annotations.

In some example embodiments, in order to optimize the performance of the machine learning model 115 performing the downstream task of image analysis, the puzzle P may be generated to include multiple imaging modalities including, for example, radiography, magnetic resonance imaging (MRI), nuclear imaging, ultrasound, elastogrpahy, photoacoustic imaging, tomography, echocardiography, functional near-infrared spectroscopy, magnetic particle imaging, and/or the like. For example, as shown in FIG. 2, the puzzle P may include a first piece corresponding to a first portion of the first image 210a having the first imaging modality (e.g., Fluid-attenuated inversion recovery (FLAIR)), a second piece corresponding to a second portion of the second image 210b having the second imaging modality (e.g., T1-weighted contrast-enhanced (T1CE) magnetic resonance imaging (MRI)), a third piece corresponding to a third portion of the third image 210c having the third imaging modality (e.g., T1-weighted magnetic resonance imaging (MRI)), and a fourth piece corresponding to a fourth portion of the fourth image 210d having the fourth imaging modality (e.g., T2-weighted magnetic resonance imaging (MRI)).

Given the set of patch sets $P=p_1, p_2, \ldots, p_N$, the machine learning model 115 (e.g., the feedforward network G) may be trained to learn the mapping from the puzzle P to the corresponding ground truth P*. For example, each element in the puzzle P may be passed through the machine learning model 115 to generate a single output feature vector having a length N before the feature vectors for every region set in the puzzle P may be concatenated to form an N×N matrix. The Sinkhorn operator may be applied to the N×N matrix to obtain the soft permutation matrix S. Moreover, the training of the machine learning model 115 (e.g., the feedforward network G) may include minimizing the mean squared error (MSE) between the ground-truth P* and the reconstructed version of the puzzle P obtained by applying the soft permutation matrix S to the puzzle P (e.g., $S^T P$).

At 404, the machine learning controller 110 may tune the machine learning model 115 trained to perform the first task on a second task of image analysis. In some example embodiments, once the machine learning model 115 is trained to perform the proxy task of puzzle solving, the machine learning controller 110 may further tune the machine learning model 115 to perform the downstream task of image analysis. The tuning of the machine learning model 115 may be performed in a supervised manner but the tuning may require a minimal quantity of labeled training data in order for the machine learning model 115 to achieve an optimal performance.

At 406, the machine learning controller 110 may deploy the machine learning model 115 to perform the second task. For example, upon being trained to perform the proxy task of puzzle solving and tuned on the downstream task of image analysis, the machine learning model 115 may be deployed to the image analysis engine 120. The machine learning model 115 may be applied to analyze, for example, the image 150 sent to the image analysis engine 120 by the client 130. For instance, the machine learning model 115 may be applied to the image 150 in order to perform tumor segmentation in which the machine learning model 115 may differentiate between the tumor and the normal tissue depicted in the image 150. Alternatively and/or additionally, the machine learning model 115 may be applied to the image 150 in order to perform survival prediction (e.g., regression) including by determining, based at least on the image 150, a quantity of time a patient associated with the image 150 is expected to survive.

Figure 5:
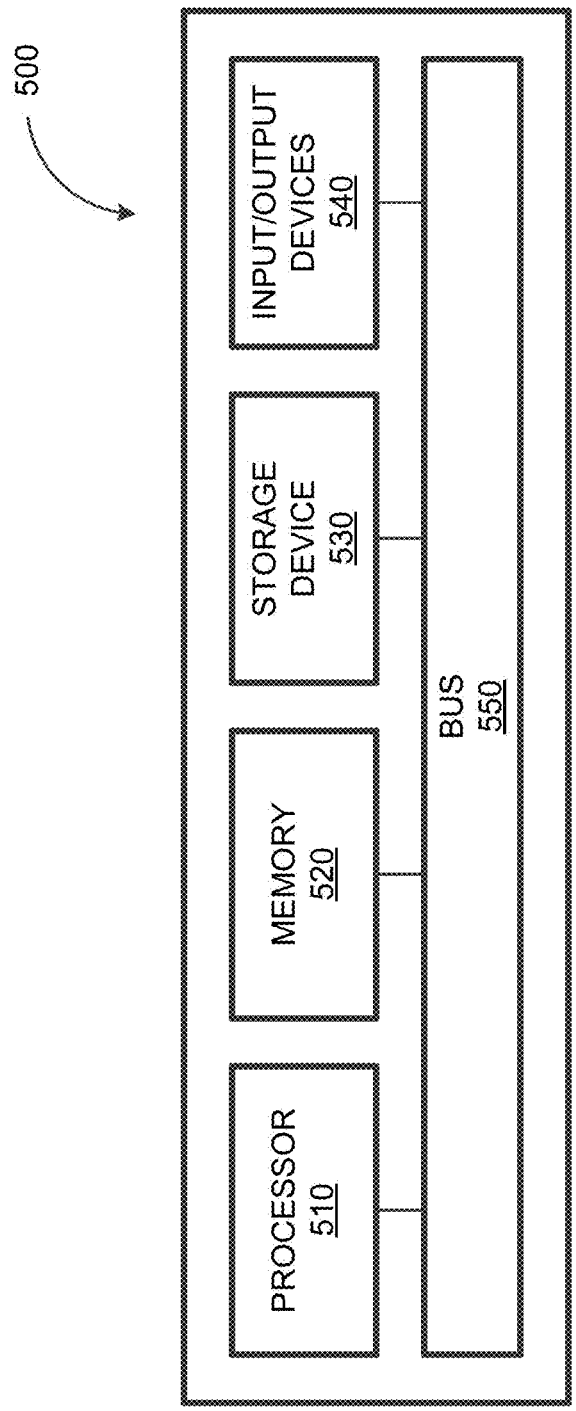
FIG. 5 depicts a block diagram illustrating a computing system, in accordance with some example embodiments.

FIG. 5 depicts a block diagram illustrating a computing system 500, in accordance with some example embodiments. Referring to FIGS. 1 and 5, the computing system 500 can be used to implement the machine learning controller 110, the image analysis engine 120, and/or any components therein.

As shown in FIG. 5, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the machine learning controller 110 and the image analysis engine 120. In some implementations of the current subject matter, the processor 510 can be a single-threaded processor. Alternately, the processor 510 can be a multi-threaded processor. The processor 510 is capable of processing instructions stored in the memory 520 and/or on the storage device 530 to display graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, or a tape device, or other suitable persistent storage means. The input/output device 540 provides input/output operations for the computing system 500. In some implementations of the current subject matter, the input/output device 540 includes a keyboard and/or pointing device. In various implementations, the input/output device 540 includes a display unit for displaying graphical user interfaces.

According to some implementations of the current subject matter, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some implementations of the current subject matter, the computing system 500 can be used to execute various interactive computer software applications that can be used for organization, analysis and/or storage of data in various (e.g., tabular) format (e.g., Microsoft Excel®, and/or any other type of software). Alternatively, the computing system 500 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities (e.g., SAP Integrated Business Planning add-in for Microsoft Excel as part of the SAP Business Suite, as provided by SAP SE, Walldorf, Germany) or can be stand-alone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. For example, the logic flows may include different and/or additional operations than shown without departing from the scope of the present disclosure. One or more operations of the logic flows may be repeated and/or omitted without departing from the scope of the present disclosure. Other implementations may be within the scope of the following claims.

What is claimed is:

1. A system, comprising:
at least one data processor; and
at least one memory storing instructions which, when executed by the at least one data processor, result in operations comprising:
training, based at least on a first training data, a machine learning model to perform a first task of puzzle solving, the first training data including a puzzle that is generated to include a first piece comprising a first portion of a first image having a first imaging modality and a second piece comprising a second portion of a second image having a second imaging modality, the first imaging modality and the second imaging modality comprising a different one of a radiography, a magnetic resonance imaging (MRI), a nuclear imaging, an ultrasound, an elastogrpahy, a photoacoustic imaging, a tomography, an echocardiography, a functional near-infrared spectroscopy, and a magnetic particle imaging, the puzzle being generated by at least shuffling a respective position of the first piece and the second piece in a third image including the first piece and the second piece, and the machine learning model being trained to generate a reconstruction of the third image by at least reassembling the first piece and the second piece in the puzzle;
tuning, based at least on a second training data, the machine learning model trained to perform the first task, the machine learning model being tuned to perform a second task of image analysis, the second task comprising a tumor segmentation task that includes differentiating between a tumor tissue and a normal tissue depicted in one or more images; and
performing the second task by at least applying the machine learning model trained on the first task and tuned on the second task.

2. The system of claim 1, wherein the third image comprises a ground-truth associated with the puzzle.

3. The system of claim 1, wherein the training of the machine learning model includes minimizing a mean squared error (MSE) between the third image and the reconstruction of the third image.

4. The system of claim 1, wherein the training of the machine learning model is self-supervised, and wherein the tuning of the machine learning model is supervised.

5. The system of claim 1, wherein the second training data includes one or more labeled training samples.

6. The system of claim 1, wherein the second task comprises an image segmentation task or a regression task.

7. The system of claim 1, wherein the second task further comprises a survival prediction task that includes determining, based at least on one or more images, a quantity of time a patient associated with the one or more images is expected to survive.

8. The system of claim 1, wherein the first task comprises a proxy task, and wherein the second task comprises a downstream task.

9. A computer-implemented method, comprising:
training, based at least on a first training data, a machine learning model to perform a first task of puzzle solving, the first training data including a puzzle that is generated to include a first piece comprising a first portion of a first image having a first imaging modality and a second piece comprising a second portion of a second image having a second imaging modality, the first imaging modality and the second imaging modality comprising a different one of a radiography, a magnetic resonance imaging (MRI), a nuclear imaging, an ultrasound, an elastogrpahy, a photoacoustic imaging, a tomography, an echocardiography, a functional near-infrared spectroscopy, and a magnetic particle imaging, the puzzle being generated by at least shuffling a respective position of the first piece and the second piece in a third image including the first piece and the second piece, and the machine learning model being trained to generate a reconstruction of the third image by at least reassembling the first piece and the second piece in the puzzle;
tuning, based at least on a second training data, the machine learning model trained to perform the first task, the machine learning model being tuned to perform a second task of image analysis, the second task comprising a tumor segmentation task that includes differentiating between a tumor tissue and a normal tissue depicted in one or more images; and
performing the second task by at least applying the machine learning model trained on the first task and tuned on the second task.

10. The method of claim 9, wherein the third image comprises a ground-truth associated with the puzzle.

11. The method of claim 9, wherein the training of the machine learning model includes minimizing a mean squared error (MSE) between the third image and the reconstruction of the third image.

12. The method of claim 9, wherein the training of the machine learning model is self-supervised, and wherein the tuning of the machine learning model is supervised.

13. The method of claim 9, wherein the second training data includes one or more labeled training samples.

14. The method of claim 9, wherein the second task comprises an image segmentation task or a regression task.

15. The method of claim 9, wherein the second task further comprises a survival prediction task that includes determining, based at least on one or more images, a quantity of time a patient associated with the one or more images is expected to survive.

16. A non-transitory computer readable medium storing instructions, which when executed by at least one data processor, result in operations comprising:
training, based at least on a first training data, a machine learning model to perform a first task of puzzle solving, the first training data including a puzzle that is generated to include a first piece comprising a first portion of a first image having a first imaging modality and a second piece comprising a second portion of a second image having a second imaging modality, the first imaging modality and the second imaging modality comprising a different one of a radiography, a magnetic resonance imaging (MRI), a nuclear imaging, an ultrasound, an elastogrpahy, a photoacoustic imaging, a tomography, an echocardiography, a functional near-infrared spectroscopy, and a magnetic particle imaging, the puzzle being generated by at least shuffling a respective position of the first piece and the second piece in a third image including the first piece and the second piece, and the machine learning model being trained to generate a reconstruction of the third image by at least reassembling the first piece and the second piece in the puzzle;

tuning, based at least on a second training data, the machine learning model trained to perform the first task, the machine learning model being tuned to perform a second task of image analysis, the second task comprising a tumor segmentation task that includes differentiating between a tumor tissue and a normal tissue depicted in one or more images; and performing the second task by at least applying the machine learning model trained on the first task and tuned on the second task.

\* \* \* \* \*